US005080650A

United States Patent [19]

Hirsch et al.

[11] Patent Number: 5,080,650

[45] Date of Patent: Jan. 14, 1992

[54] GASTROSTOMY TUBE

[75] Inventors: William H. Hirsch, Columbus, Ohio; Kent E. Iversen, Freehold, N.J.

[73] Assignee: Abbott Laboratories, Abbott Park, Ill.

[21] Appl. No.: 646,030

[22] Filed: Jan. 28, 1991

[51] Int. Cl.[5] .............................................. A61M 29/00

[52] U.S. Cl. ........................................ 604/104; 604/54

[58] Field of Search ............... 604/264, 270, 104, 105, 604/106, 174, 175, 280, 93, 54

[56] References Cited

U.S. PATENT DOCUMENTS

| | | | |
|---|---|---|---|
| 3,397,699 | 8/1968 | Kohl | 604/105 |
| 4,668,225 | 5/1987 | Russo et al. | 604/270 |
| 4,758,219 | 7/1988 | Sacks et al. | 604/54 |

OTHER PUBLICATIONS

Fouch et al., "A Critical Analysis of the Sacks-Vine Gastrostomy Tube A Review of 120 Consecutive Procedures", *The American Journal of Gastroenterolgy*, Aug. 1988, pp. 812-815.

Rombeau et al., *Atlas of Nutritional Support Techinques*, Little, Brown and Company, 1989, pp. 132-136.

*Primary Examiner*—John D. Yasko

*Attorney, Agent, or Firm*—Lonnie R. Drayer; Donald O. Nickey

[57] ABSTRACT

A gastrostomy tube has a retaining element which has a generally triangular shape with rounded vertices. The retaining element is made up of three resilient petaloid flanges which extend radially from the tubular portion of the gastrostomy tube. The petaloid flanges and the tubular portion are made of different materials. Substantially triangular connecting portions are interposed between and interconnect each pair of next adjacent petaloid flanges. The petaloid flanges are rendered less flexible than the connecting portions by either variations in thickness or materials between the petaloid flanges and connecting portions. The assembly of a gastrostomy tube and a tapered dilator is also disclosed.

15 Claims, 5 Drawing Sheets

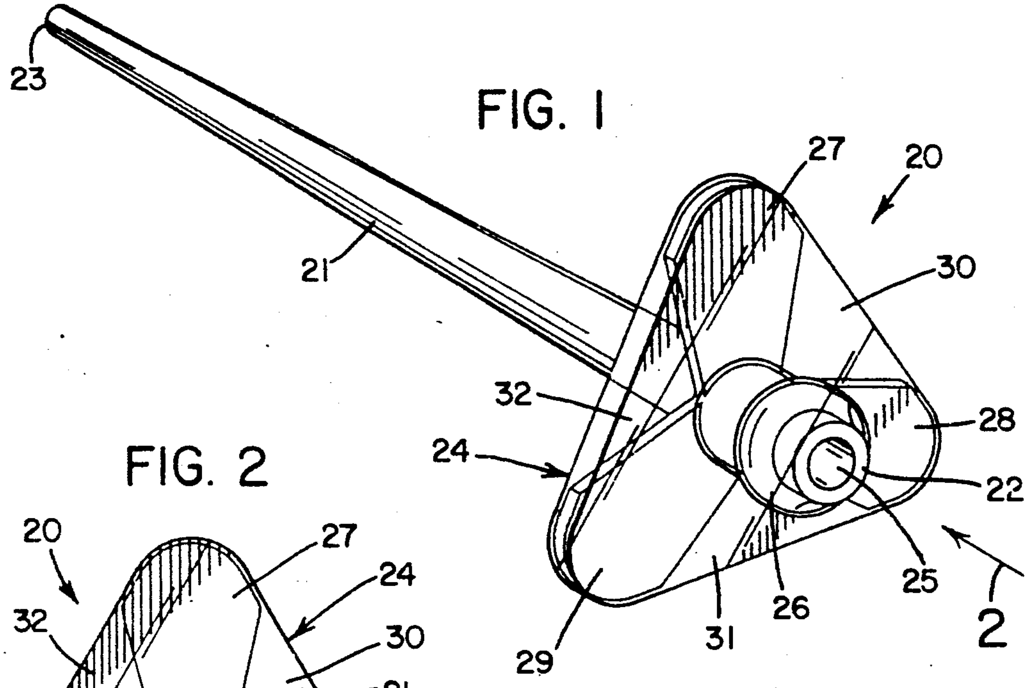
FIG. 1
FIG. 2
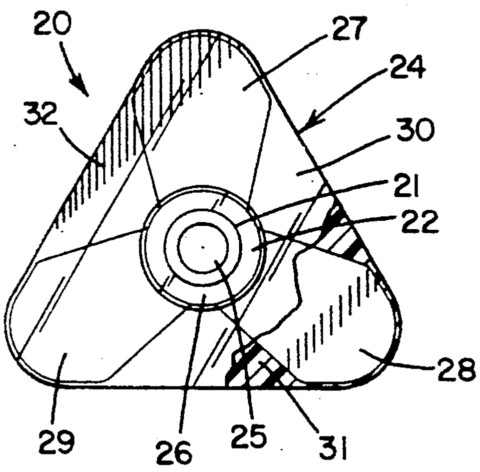
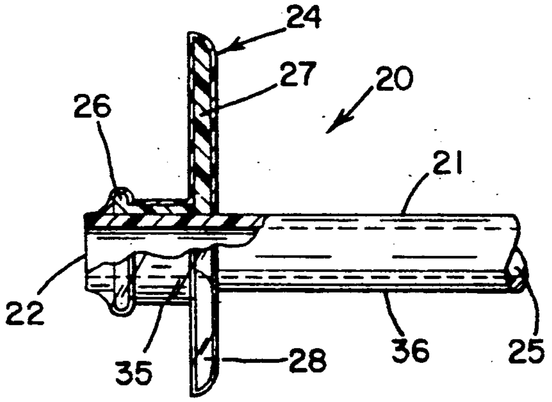
FIG. 3
FIG. 4
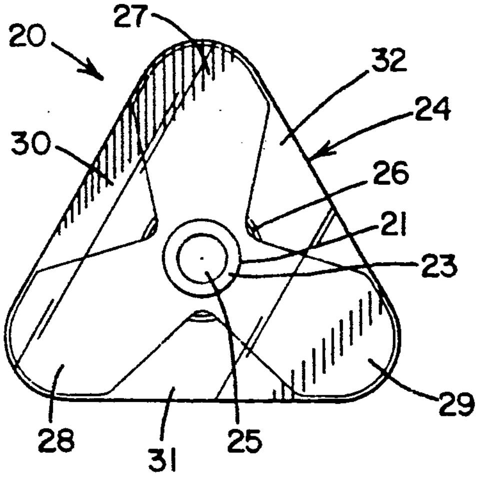
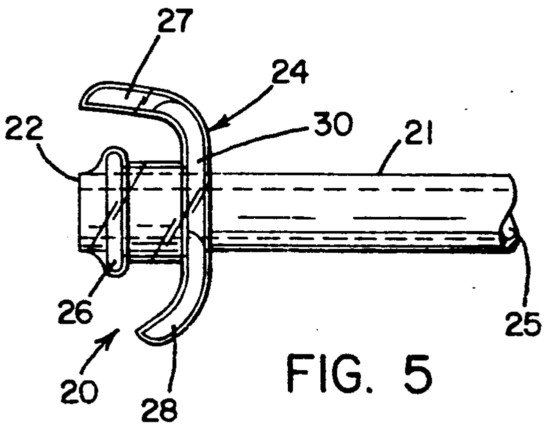
FIG. 5

FIG. 6
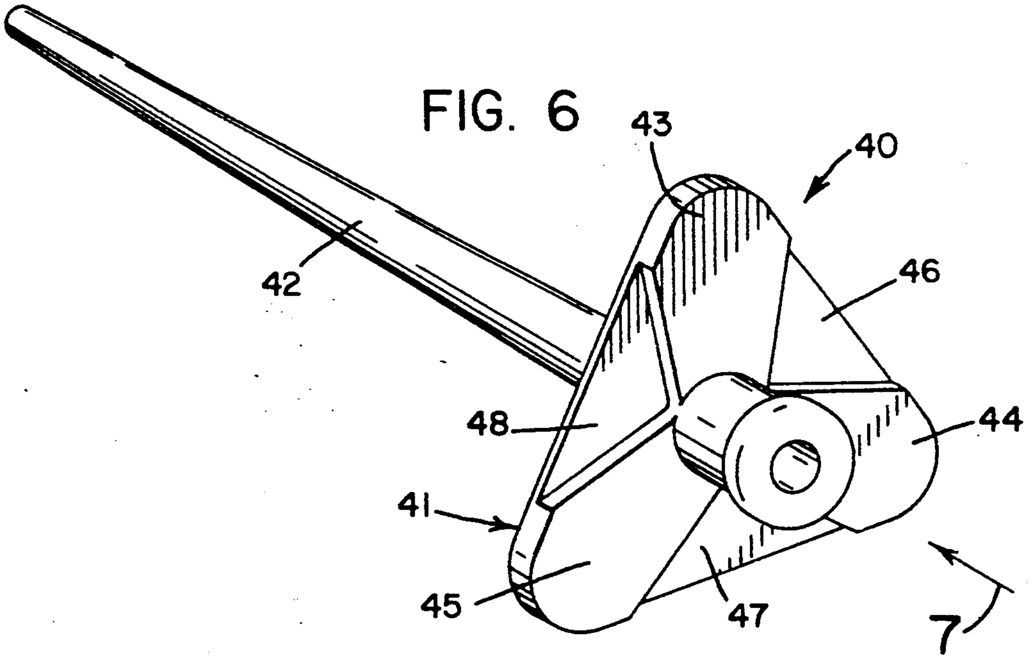
FIG. 7
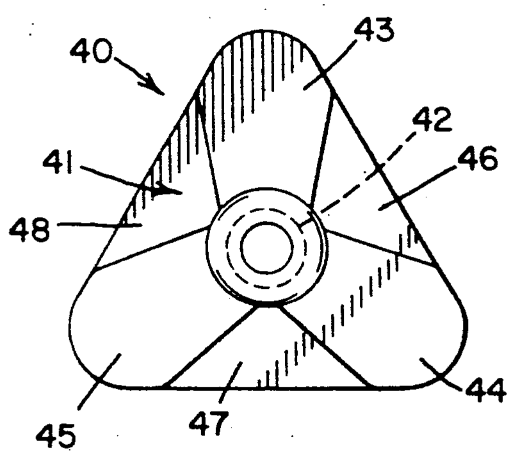
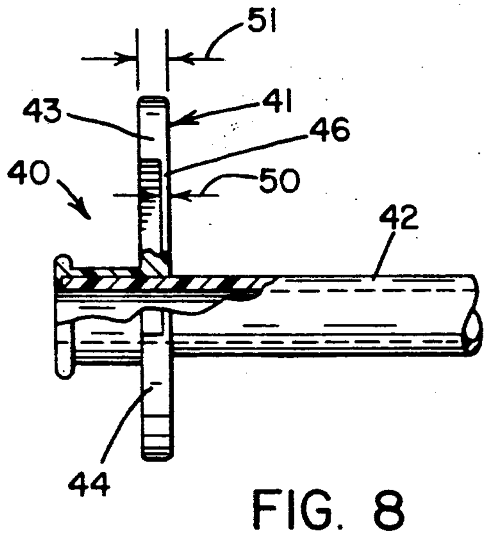
FIG. 8
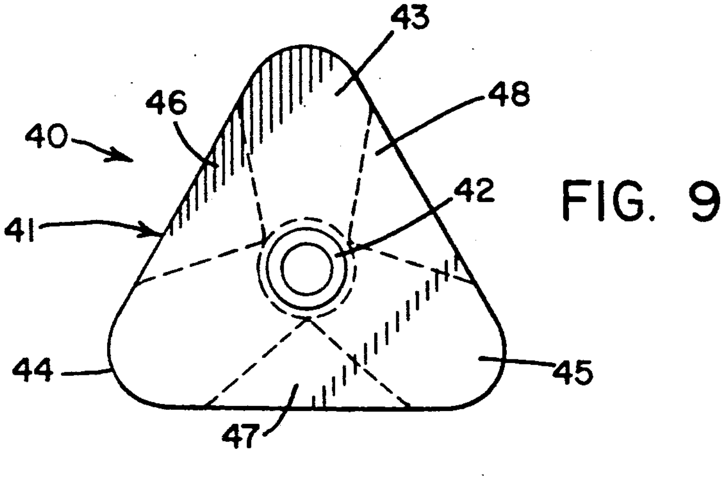
FIG. 9

GASTROSTOMY TUBE

The present invention relates to a gastrostomy tube, and more particularly to a gastrostomy tube which can accommodate internal passage therethrough of a feeding tube.

A surgical procedure wherein an opening is formed in the skin, fascia and stomach wall and a tube is installed in the opening to allow nutrition to be provided directly into the stomach or intestines is known as a gastrostomy. A tube which is inserted through the opening made during the surgical procedure to maintain the opening is known as a gastrostomy tube. Examples of individuals who would require such a procedure include burn patients, whose daily caloric needs are very high; critically ill, weak or comatose patients who may be unable to chew their food; and patients suffering from a diseased or traumatized esophagus, who may be unable to swallow food.

The gastrostomy tube of the present invention is adapted for placement in a patient using the Sacks-Vine procedure, sometimes referred to as a "push" procedure. Briefly, this procedure entails the following steps: (a) passing an endoscope through the esophagus into the stomach; (b) locating a suitable site for the gastrostomy; (c) passing a Seldinger needle through the abdominal wall into the stomach, removing the inner stylet and leaving the outer cannula in place, then inserting a snare via the endoscope and looping the snare over the end of the cannula; (d) inserting a guidewire through the Seldinger Needle into the stomach, grasping the guidewire via the snare, and withdrawing the endoscope to deliver the guidewire through the mouth; (e) advancing the gastrostomy tube over the guidewire until the gastrostomy tube reaches the cannula and pushes the cannula through the abdominal wall; (f) gently pulling the gastrostomy tube through the abdominal wall until the retaining element of the tube engages the gastric mucosa; and (g) securing the gastrostomy tube in place by sliding a retention disc over the portion of the gastrostomy tube which now protrudes through the patient's abdomen, and then cutting off the excess length of the gastrostomy tube. The Sacks-Vine procedure is well known, and has been described for example in THE AMERICAN JOURNAL OF GASTROENTEROLOGY ("A CRITICAL ANALYSIS OF THE SACKS-VINE GASTROSTOMY TUBE A REVIEW OF 120 CONSECUTIVE PROCEDURES", P. G. Foutch, et. al., THE AMERICAN JOURNAL OF GASTROENTEROLOGY, August 1988, Pages 812–815) and books such as ATLAS OF NUTRITIONAL SUPPORT TECHNIQUES, John L. Rombeau, et. al, Little, Brown and Company, 1989, Pages 132–136.

U.S Pat. No. 4,758,219 teaches a gastrostomy tube and an assembly of a dilator and a gastrostomy tube. The actual retaining element is a separate piece of tubing which is affixed such that it extends perpendicular to the axis of the gastrostomy tube. The retaining element of the gastrostomy tube is secured in place by a multi-wing releasable lock formed from the wall of the gastrotomy tube by slitting the tube longitudinally over a predetermined length at a selected number of points about the circumference of the tube. A special instrument must be inserted into the gastrostomy tube to unlock the locking mechanism when the gastrostomy tube is removed from a patient, and the short piece of tubing that serves as the retaining element is separated from the gastrostomy tube at that time. This prior art device has only the tubular retaining element to seal the stoma against leakage, and will necessarily have a higher contact pressure against the stomach mucosa than the retaining element of the gastrostomy tube disclosed herein.

There are, of course, other accepted procedures for performing a gastrostomy, and inserting a gastrostomy tube. For example, U.S. Pat. No. 4,668,225 teaches a gastrostomy tube which is adapted for insertion into the stomach through an incision in a patient's abdomen. The retaining element of the gastrostomy tube taught in this document comprises a plurality of resilient flanges which are interconnected by hub portions which extend outwardly from the tube a lesser distance than the flanges, however; this gastrostomy tube leaves unsolved the problems of premature tube removal and migration of the retaining element and tube out of the stomach into the fasciae, thus allowing the stomach to no longer be in opposition to the abdominal wall. This can result in leakage of gastric contents, or direct feeding of a nutritional product into the peritoneum with the possible onset of peritonitis. This problem is overcome by a gastrostomy tube according to the present invention by providing a retaining element with significantly more surface area than the prior art retaining element, thereby decreasing pressure on the stomach wall while maintaining the gastrostomy tube in the desired position thus decreasing the probability of gastric exchange through the stoma site.

BRIEF DESCRIPTION OF THE DRAWINGS

FIGS. 1–5 show a gastrostomy tube according to a first embodiment of the invention.

FIGS. 6–9 show a gastrostomy tube according to a second embodiment of the invention.

DETAILED DESCRIPTION OF THE INVENTION

Figure 10:
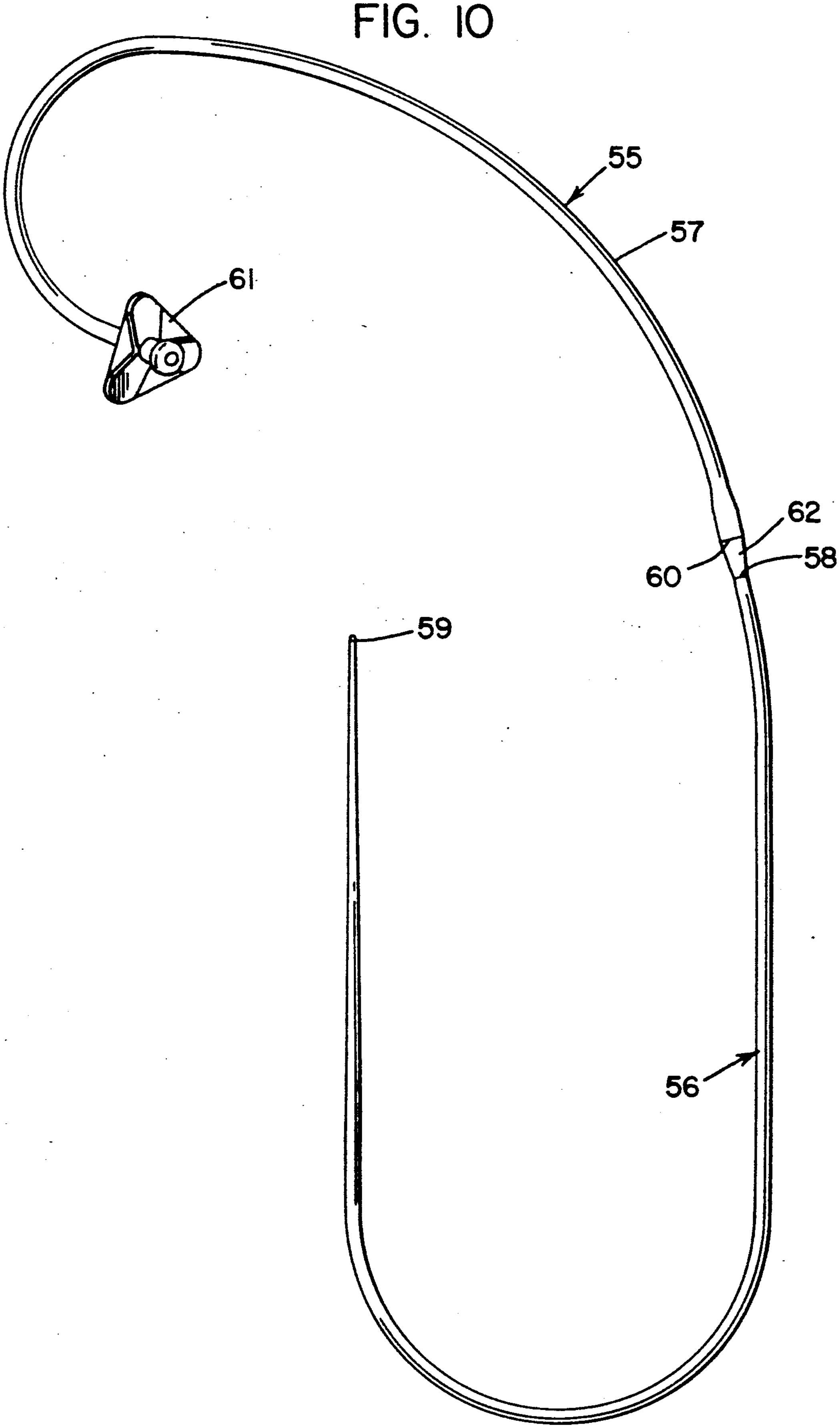
FIG. 10 shows an assembly of a gastrostomy tube, according to the second embodiment, and a tapered dilator.

Referring first to FIGS. 1–5 there is shown a gastrostomy tube according to a first embodiment of the invention. FIG. 1 is a perspective view; FIG. 2 is a front elevation view looking in the direction indicated by arrow 2 in FIG. 1; FIG. 3 is a side elevation view, partially broken away; FIG. 4 is a rear elevation view; and FIG. 5 is a partial side elevation view with the retaining element partially folded over onto itself.

A gastrostomy tube 20 according to the invention comprises a tubular portion 21 having first and second ends 22, 23 and a retaining element 24 disposed near the first end 22 of the tubular portion. A lumen 25 extends from the first end to the second end of the tubular portion. The section 35 of the tubular portion which is disposed between the first end 22 of the tubular portion 21 and the retaining element 24 has a larger outside diameter and wall thickness than the remainder of the length of the tubular portion. In a working example the outside diameter of a first section 35 of the tubular portion 21 which is disposed between the first end 22 and the retaining element 24 has an outside diameter of about 8.8 mm (0.345 inch), and a second section 36 of the tubular portion disposed between the second end 23 and the retaining element 24 has an outside diameter of about 6.2 mm (0.246 inch), which diameter is commonly referred to as size eighteen French. The lumen 25 has a diameter which is constant along the entire length of the tube, and in the working example that diameter is about 4.5 mm (0.176 inch). As a result, the thickness of the wall of the tubular portion is about 141% greater in the first section 35 of the tubular portion than in the second section 36. A circular collar 26 is located at or near the first end 22 of the tubular portion 21 and functions in cooperation with the thick section 35 of the tubular portion as a site which an endoscopist may snare when the gastrostomy tube is removed, and extracted through the patients' esophagus.

In each embodiment of the invention the retaining element 24 comprises three resilient petaloid flanges 27, 28, 29 which extend radially from the tubular portion 21. As used herein and in the claims "petaloid" is understood to mean a shape resembling a flower petal, being narrowest at its junction with the tubular portion then becoming wider and then narrower at the portion of the flange which is distal from the tubular portion. Substantially triangular connecting portions 30, 31, 32 are interposed between each pair of next adjacent petaloid flanges, and function in part to connect the petaloid flanges to one another. It is to be noted that in the specific embodiment illustrated in FIGS. 1-5 the petaloid flanges 27, 28, 29 comprise an opaque material while the connecting portions 30, 31, 32 comprise a transparent material which also encases the petaloid flanges. It is understood however that any combination of two transparent, two opaque, or one of each type of material may be employed in this embodiment subject only to other properties of the materials which will be described later. The ends of the petaloid flanges which are distal from the tubular portion are rounded, and the petaloid flanges and connecting flanges are shaped such that the retaining element 24 in front or rear elevation (as shown in FIGS. 2, 4, 7 and 9) has a triangular shape with rounded vertices.

It is an important feature of a gastrostomy tube according to the invention that in the retaining element 24 the petaloid flanges 27, 28, 29 are less flexible than the connecting portions 30, 31, 32. This feature allows the retaining element to collapse towards the tubular portion as illustrated in FIG. 5 such that the retaining element 24 may pass through the esophagus of a patient more easily, while at the same time allowing the retaining element to have a greater surface area for contacting the lining of the patient's stomach when the gastrostomy tube is in its operative position. If the retaining element were to comprise only the petaloid flanges it could still pass through the esophagus, but would have a smaller contact area with the stomach lining and thus a higher pressure per unit of contact area. If the flexibility of the retaining element was uniform throughout, the retaining element might not fold over properly or might not spring back to being perpendicular to the tubular portion after the retaining element leaves the esophagus and enters the stomach.

In the embodiment illustrated in FIGS. 1-5 the variation in flexibility between the petaloid flanges 27, 28, 29 and the connecting portions 30, 31, 32 is obtained by having the petaloid flanges 27, 28, 29 comprise a first material and the connecting portions of the retaining element comprise a second material. In the embodiment illustrated in FIGS. 1-5 the petaloid flanges are encased in the material which comprises the connecting flanges due to a two stage molding process, but the overall thickness of the retaining element is substantially uniform. However; it is understood the thickness of the petaloid flanges and the connecting portions may be substantially the same, or that the connecting portions may have a thickness that is less than the thickness of the petaloid flanges.

In the embodiment illustrated in FIGS. 1-5, as well as the embodiment illustration in FIGS. 6-9 which will be described later, the petaloid flanges of the retaining element are preferably made of a material having a durometer in the range of 50 to 80 Shore A, and which is more preferably selected from the group consisting of silicone rubbers, polyurethanes and polyvinyl chloride. Most preferably the material is a medical grade silicone rubber having a Shore A durometer that is in the preferred range of 50 to 80. As used herein and in the claims a medical grade material is understood to mean a material that is approved by the Food and Drug Administration of the Federal Government of The United States of America for food contact and meets United States Pharmacopeia (U.S.P) class VI testing for biocompatibility. For example, gastrostomy tubes in accordance with the present invention have been manufactured having the petaloid flanges of the retaining element comprising Q7-4765 silicone Silastic® Medical Grade ETR Elastomer which is available from Dow Corning Corporation. The connecting portions 30, 31, 32 of the retaining element of the embodiment illustrated in FIG. 1-5 preferably comprise a material having a durometer in the range of 10 to 40 Shore A which is more preferably selected from the group consisting of silicone rubbers, polyurethanes and polyvinyl chloride. Most preferably the material is a medical grade silicone rubber having a durometer that is in the preferred range of 10 to 40 Shore A. Preferably, the petaloid flanges of the retaining element comprise a material containing barium sulfate in order to render this portion of the gastrostomy tube radiopaque so that it will show up in an x-ray of the patient.

It is now believed to be an important feature of a gastrostomy tube according to all embodiments the invention described herein that between the retaining element 24 and the second end 33 of the tubular portion, in other words the second section 36 of the tubular portion, comprises a material having a durometer in the range of 30 to 40 Shore A, most preferably about 35 Shore A. Preferably this section of the tubular portion comprises a material selected from the group consisting of silicone rubbers, polyurethanes and polyvinyl chloride. Most preferably the material is a medical grade silicone rubber. Preferably this section of the tubular portion comprises a material which contains a suitable amount (for example 1%) of titanium dioxide as a coloring agent. Inasmuch as the petaloid flanges of the retaining element and the tubular portion comprise different materials, these components may be attached to one another by a suitable adhesive, but preferably are insert molded together.

An explanation of the criticality of using materials of such varying durometer values in the retaining element and the tubular portion has only recently been recognized. During about the first fourteen days following the insertion of the gastrostomy tube via the Sacks Vine procedure, the opening through the patient's abdominal wall has not yet become lined with scar tissue. If the patient should pull on the gastrostomy tube with sufficient force during this critical scar forming period, the retaining element could be pulled through the stomach lining but not through the skin, therefor allowing contamination of the peritoneum. Up to a limit, the lower durometer material of the tubular portion will dissipate the pulling force exerted by the patient, but if this limit is passed by the patient pulling excessively hard on the tube the retaining element will be pulled completely through to the exterior of the patients skin. However; the retaining element does need to be made of a higher durometer material so that it will be rigid enough to maintain the tube in place and form a seal with the stomach lining under normal circumstances.

Referring next to FIGS. 6–9 there is shown a gastrostomy tube according to a second embodiment of the invention. FIG. 6 is a perspective view; FIG. 7 is a front elevation view looking in the direction indicated by arrow 7 in FIG. 6; FIG. 8 is a side elevation view, partially in section; and FIG. 9 is a rear elevation view.

A gastrostomy tube 40 according to this second embodiment is substantially like the first embodiment shown in FIGS. 1–5 except for the structure of the retaining element 41. That is to say this embodiment has a tubular portion 42, and a retaining element 41 comprising petaloid flanges 43, 44, 45 and connecting portions 46, 47, 48.

As already stated it is an important feature of a gastrostomy tube according to the invention that in the retaining element the petaloid flanges are less flexible than the connecting portions. In the embodiment illustrated in FIGS. 6–9 the entire retaining element comprises a single material, and the necessary variation in flexibility is obtained by the connecting portions 46, 47, 48 having a thickness 50 that is less than the thickness 51 of the petaloid flanges. Gastrostomy tubes have been successfully manufactured wherein the petaloid flanges 43, 44, 45 have specified thickness 50 of about 0.2 mm (0.08 inch) and the connecting portions 46, 47, 48 have a specified thickness 51 of about 0.5 mm (0.02 inch), such that the thickness of the petaloid flanges is about four times greater than the thickness of the connecting portions. However; it is believed that functional gastrostomy tubes may be manufactured wherein the thickness of the petaloid flanges is in the range of two times to six times greater than the thickness of the connecting portions, depending upon the material of which the gastrostomy tube is comprised. In all other respects a gastrostomy tube according to this embodiment is substantially like the embodiment of FIGS. 1–5.

In the embodiment illustrated in FIGS. 6–9 the entire retaining element is made of a single material having a durometer in the range of 50 to 80 Shore A, and is selected from the group consisting of silicones, polyurethanes and polyvinyl chlorides. Most preferably the material is a medical grade silicone rubber having a durometer that is in the preferred range and contains barium sulfate in order to render the retaining element radiopaque so that it will show in an x-ray of the patient.

Referring next to FIG. 10, there is shown an assembly comprising a gastrostomy tube 55 and a tapered dilator 56. The gastrostomy tube illustrated in FIG. 10 is like the embodiment illustrated in FIGS. 6–9, but it is understood that a gastrostomy tube according to the embodiment shown in FIGS. 1–5 may also be used in the assembly in place thereof. If the tubular portion 57 of the gastrostomy tube 55 were to comprise a material of sufficient rigidity, it could be configured to function as a dilator. However; inasmuch as the preferred materials for the tubular portion of the gastrostomy tube are fairly soft and flexible, it is preferred that the dilation of the passage through the stomach and abdominal wall which is formed by a Seldinger needle during the Sacks-Vine procedure is better accomplished by using a tapered dilator 56 of a more rigid material. That is to say, the tubular portion 57 of the gastrostomy tube 55 should comprise a first material and the tapered dilator 56 should comprise a second material, with the first material having a durometer that is less than the durometer of the second material. Inasmuch as the tubular portion of the gastrostomy tube comprises a material having a durometer in the range of 30 to 40 Shore A, it is preferred that the tapered dilator comprise a low or medium density polyethylene. As used herein and in the claims a low density polyethylene is understood to have a density in the range of 0.90 to 0.92 gm/cm$^3$ and a medium density polyethylene is understood to have a density in the range of 0.92 to 0.94 gm/cm$^3$. Assemblies have been manufactured wherein the tubular portion of the gastrostomy tube is a medical grade silicone rubber and the tapered dilator comprises a low or medium density polyethylene. Other materials believed to be suitable for the tapered dilator are nylons and polyolefins.

The tapered dilator 56 has first and second ends 58, 59 with a lumen extending between the ends of the dilator. The outside diameter of the dilator is greater at the first end 58 of the dilator than at the second end 59 of the dilator. The first end 58 of the tapered dilator is connected by means for connecting 62 to the end 60 of the tubular portion 57 of the gastrostomy tube that is most distant from the retaining element 61 of the gastrostomy tube. The means for connecting may be integral to the tapered dilator, for example a barbed portion located near the first end 58 of the tapered dilator. However; if as in a commercial embodiment of the assembly the tubular portion of the gastrostomy tube comprises a medical grade silicone rubber and the tapered dilator comprises a low density polyethylene, it is preferred that the means for connecting be a hollow tubular connector 62 comprising a third material. Satisfactory assemblies have been manufactured employing a barbed tubular connector made of nylon. The significance of this particular combination of materials for the components of the assembly is that it facilitates the fastening together of components made of dissimilar materials so that the assembly is sufficiently strong and will not separate during the placement procedure.

Figure 11:
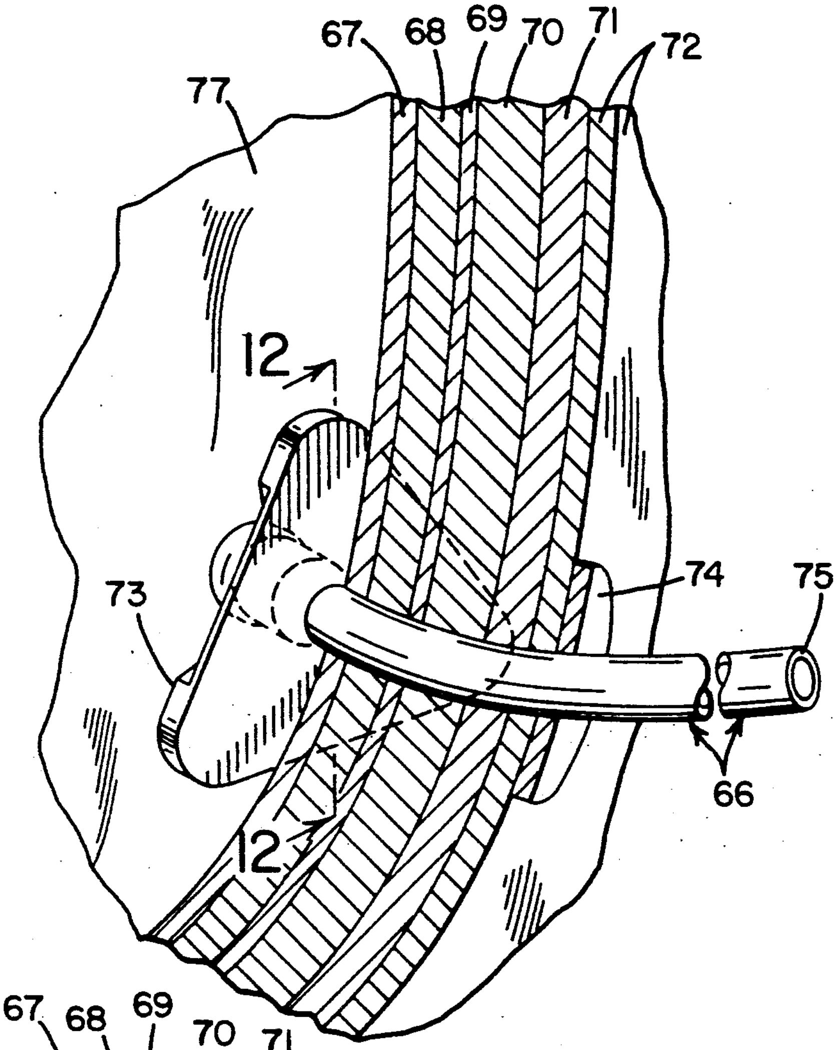
FIGS. 11 and 12 show a gastrostomy tube according to the invention placed into a stomach and extending through a stoma.
Figure 12:
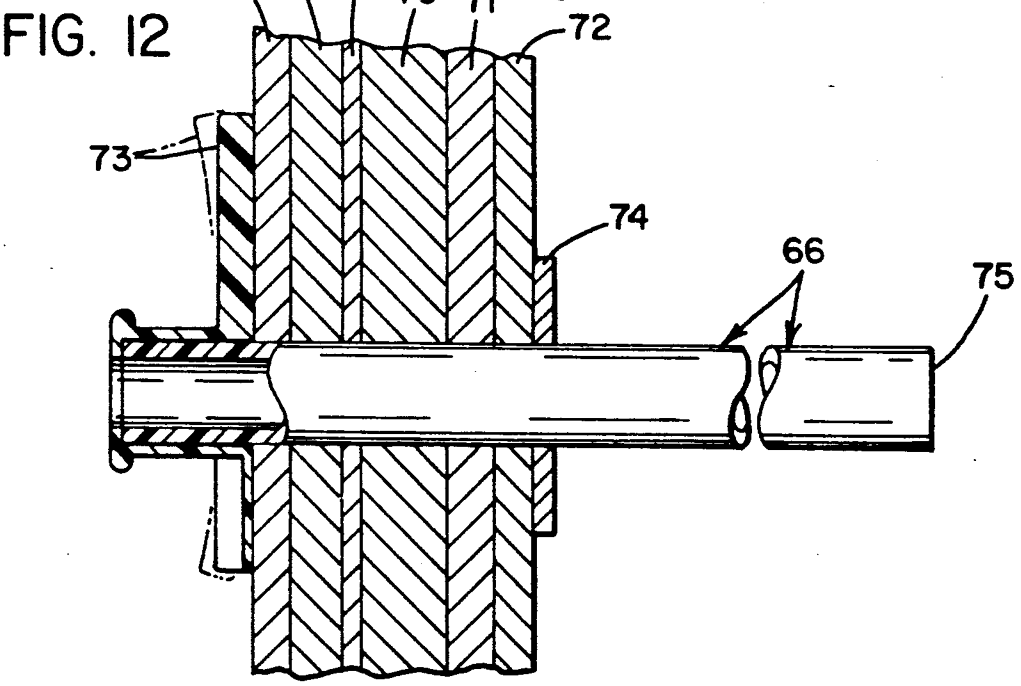
Figure 13:
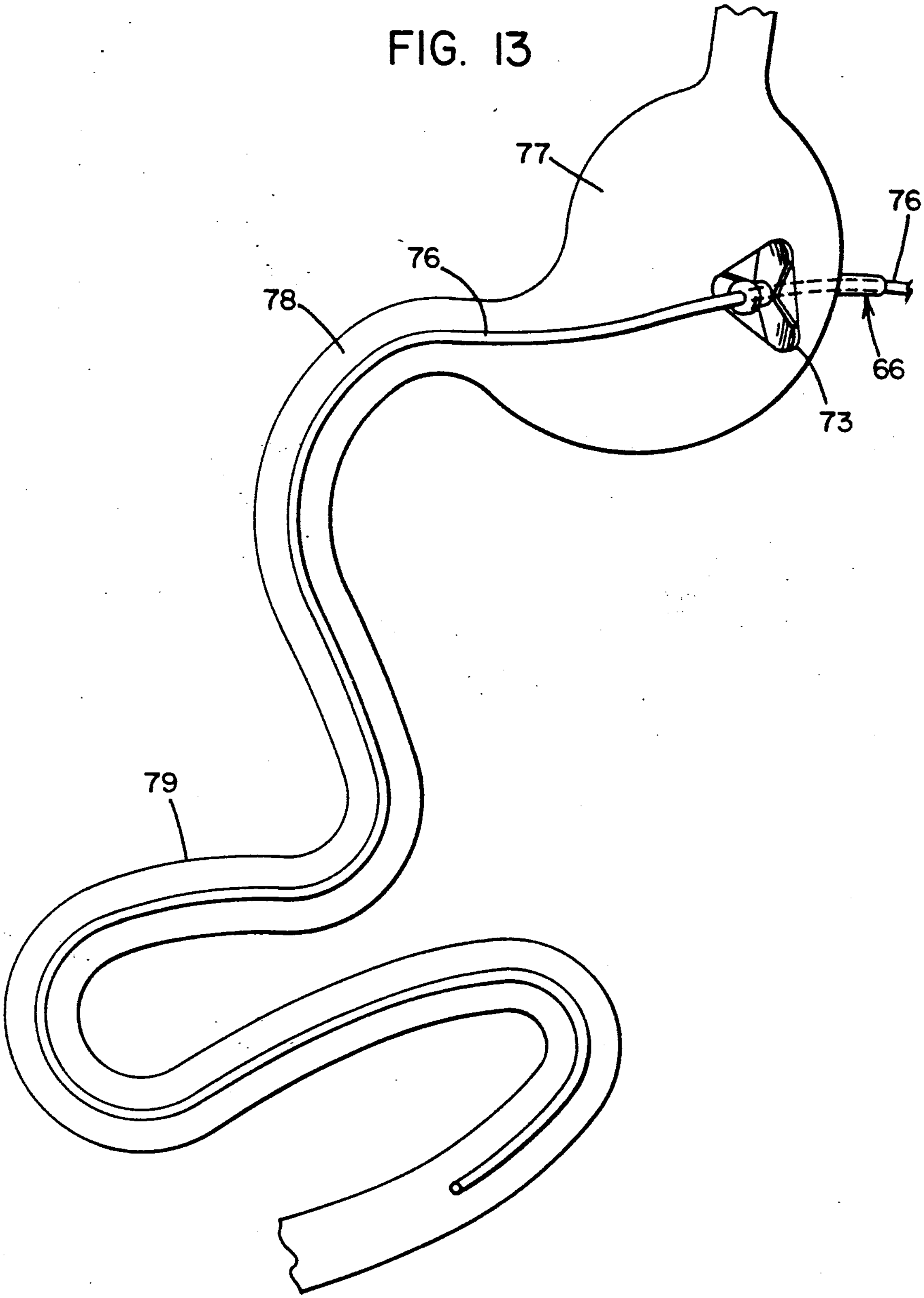
FIG. 13 shows a diagrammatic representation of a gastrostomy tube according to the invention being used in conjunction with a jejunal feeding tube.

Referring now to FIGS. 11–13 the function of a gastrostomy tube 66 according to the invention after it has been placed into a patient can be better described. The tubular portion of the gastrostomy tube 66 extends via the stoma through the mucosa wall 67, the stomach lining 68, the peritoneum 69, the muscle layer 70, the fat layer 71 and the skin 72. The retaining member 73 of the gastrostomy tube comes into contact with the mucosa wall 67 thereby forming a sealing mechanism for the stoma. A retention disk 74 has been slid over the tubular portion of the gastrostomy tube to contact the skin 72. Cooperation between the retaining member 73 of the gastrostomy tube and the retention disk 74 places the proper tension on the gastrostomy tube and reduces the probability of the undesirable movement of the gastrostomy tube further into the stomach or the unintentional withdrawal of the gastrostomy tube through the stoma.

In a preferred embodiment the tubular portion of the gastrostomy tube has graduations (not shown) on the tubular portion which may be used to confirm that the tube has not been displaced.

As best shown in FIG. 12, wherein the retaining member is shown partially in section along line 12—12 of FIG. 11, the flexible nature of the retaining element 73 allows it to better conform to the contour of the mucosa wall 67, thereby better performing its' sealing function with respect to the stoma.

As shown in FIG. 11-13 the excess length of the gastrostomy tube is cut off to form an end 75 which is located about 15 cm from the skin.

Feeding of the patient may then commence by passing a feeding tube 76 through the lumen of the gastrostomy tube 66 as shown in FIG. 13. The feeding tube shown is of the type commonly known as a jejunal tube. The jejunal tube 76 passes through the gastrostomy tube 66 into the stomach 77, thence through the stomach, past the pylorus and into the small bowel. Once in the small bowel, the jejunal tube 76 passes through the duodenum 78 and preferably terminates in the area of the jejunum 79. Feeding of the patient can thereafter be accomplished using procedures that are well known in the medical arts.

While the forms of the apparatus described herein constitute preferred embodiments of the invention, it is to be understood that the invention is not limited to this precise form of apparatus and that changes may be made therein without departing from the scope of the invention as set forth in the appended claims.

What is claimed is:

1. A gastrostomy tube comprising a tubular portion having first and second ends and a retaining element disposed near the first end of the tubular portion, said retaining element comprising three resilient petaloid flanges which extend radially from the tubular portion with substantially triangular connecting portions interposed between and connecting each pair of next adjacent petaloid flanges, the ends of the petaloid flanges which are distal from the tubular portion being rounded, the petaloid flanges and connecting portions being shaped such that said retaining element has a triangular shape with rounded vertices, and said petaloid flanges being less flexible than said connecting portions, between the retaining element and said second end the tubular portion comprises a material having a durometer in the range of 30 to 40 Shore A and the petaloid flanges of the retaining element comprise a material having a durometer in the range of 50 to 80 Shore A.

2. A gastrostomy tube according to claim 1 wherein and the entire retaining element comprises the same material, and said connecting portions have a thickness that is less than the thickness of the petaloid flanges.

3. A gastrostomy tube according to claim 2 wherein the thickness of the petaloid flanges is in the range of two times to six times greater than the thickness of said connecting portions.

4. A gastrostomy tube according to either one of claims 2 or 3 wherein both the retaining element and tubular portion comprise medical grade silicone rubbers.

5. A gastrostomy tube according to claim 1 wherein the petaloid flanges of said retaining element comprise a first material and the connecting portions of said retaining element comprise a second material that is different from the first material.

6. A gastrostomy tube according to claim 5 wherein the thickness of the petaloid flanges and the connecting portions are substantially the same.

7. A gastrostomy tube according to claim 5 wherein the petaloid flanges are encased in the material which comprises the connecting portions.

8. A gastrostomy tube according to claim 5 wherein the connecting portions have a thickness that is less than the petaloid flanges.

9. A gastrostomy tube according to any one of claims 5 to 8 wherein the connecting portions comprise a material having a durometer in the range of 10 to 40 Shore A.

10. A gastrostomy tube according to any one of claims 5 to 8 wherein the tubular portion and the petaloid flanges comprise medical grade silicone rubbers and the connecting portions comprise a medical grade silicone rubber having a durometer in the range of 10 to 40 Shore A.

11. An assembly of a gastrostomy tube and a tapered dilator comprising;

(a) a gastrostomy tube comprising a tubular portion having first and second ends and a retaining element disposed near the first end of the tubular portion, said retaining element comprising three resilient petaloid flanges which extend radially from the tubular portion with substantially triangular connecting portions interposed between and connecting each pair of next adjacent petaloid flanges, the ends of the petaloid flanges which are distal from the tubular portion being rounded, the petaloid flanges and connecting portions being shaped such that said retaining element has a triangular shape with rounded vertices, and said petaloid flanges being less flexible than said connecting portions, between the retaining element and said second end the tubular portion comprises a material having a durometer in the range of 30 to 40 Shore A and the petaloid flanges of the retaining element comprise a material having a durometer in the range of 50 to 80 Shore A; and, (b) a tapered dilator having first and second ends with a lumen extending between said ends of the dilator, the outside diameter of the dilator being greater at said first end than at said second end, the second end of the gastrostomy tube being connected to the first end of the dilator by means for connecting, the tubular portion of the gastrostomy tube comprising a first material and the dilator comprising a second material.

12. An assembly of a gastrostomy tube and a tapered dilator according to claim 11 wherein said means for connecting is integral to said tapered dilator.

13. An assembly of a gastrostomy tube and a tapered dilator according to claim 11 wherein said means for connecting is a hollow tubular connector comprising a third material.

14. An assembly of a gastrostomy tube and a tapered dilator according to claim 11 wherein said first material has a durometer in the range of 30 to 40 Shore A and said second material has a durometer that is the range of 0.90 $gm/cm^3$ to 0.94 $gm/cm^3$.

15. An assembly of a gastrostomy tube and a tapered dilator according to claim 13 wherein said first material is a medical grade silicone rubber, said second material is a low density polyethylene and said third material is a nylon.

* * * * *

UNITED STATES PATENT AND TRADEMARK OFFICE
CERTIFICATE OF CORRECTION

PATENT NO. : 5,080,650

DATED : Jan. 14, 1992

INVENTOR(S) : William H. Hirsch and Kent E. Iversen

It is certified that error appears in the above-identified patent and that said Letters Patent is hereby corrected as shown below: On the Title page, Reference Cited, item [56] "Gastroenterolgy" to --Gastroenterology--
Column 1 Line 62 "gastrotomy" to --gastrostomy--

Signed and Sealed this

Twenty-fifth Day of May, 1993

*Attest:*

MICHAEL K. KIRK

*Attesting Officer*

*Acting Commissioner of Patents and Trademarks*